US005454840A

United States Patent [19]
Krakovsky et al.

[11] Patent Number: 5,454,840
[45] Date of Patent: Oct. 3, 1995

[54] POTENCY PACKAGE

[76] Inventors: Alexander A. Krakovsky, 2500 Torrey Pines Rd. #205, La Jolla, Calif. 92037; Nikolai I. Tankovich, 9361 Stargaze Ave., San Diego, Calif. 92129

[21] Appl. No.: 223,160
[22] Filed: Apr. 5, 1994
[51] Int. Cl.$^6$ ............................................. A61N 1/36
[52] U.S. Cl. ............................................. 607/39
[58] Field of Search ........................ 607/39, 2, 40, 607/41, 143, 138; 600/33, 38, 40

[56] References Cited

U.S. PATENT DOCUMENTS

| | | | |
|---|---|---|---|
| 3,403,684 | 10/1968 | Stiebel et al. | 607/138 |
| 3,870,051 | 3/1975 | Brindley | 607/41 |
| 4,406,288 | 9/1983 | Horwinski et al. | 607/41 |
| 4,542,753 | 9/1985 | Brenman et al. | 607/138 |
| 4,564,024 | 1/1986 | Wohler, Jr. | 607/138 |
| 4,585,005 | 4/1986 | Lue et al. | 607/39 |
| 5,063,914 | 11/1991 | Cowen | 600/40 |
| 5,199,430 | 4/1993 | Fang et al. | 607/40 |

Primary Examiner—William E. Kamm
Assistant Examiner—Kennedy J. Schaetzle
Attorney, Agent, or Firm—John R. Ross

[57] ABSTRACT

A device and method for impotence correction. A device is implanted inside the body. It is programmable and controllable from outside the body. The press of a button sends a signal which initiates a process which simulates the body's natural reproductive processes. In a preferred embodiment, a programmable electronic device is implanted under abdominal muscle rectus. An electrical conductor is fixed to the surface of the pelvic splanchnic nerve. Stimulation of this nerve by low voltage electrical pulses from the electronic device causes neuromediators release which causes penis arterioles dilation which initiates erection. The electronic device is controlled by a controller operated by the patient or his partner. A second preferred embodiment also provides for emission stimulation. Emission is stimulated by electrical excitation of the pelvic plexus nerves from separate conductors from the electronic device.

14 Claims, 7 Drawing Sheets

POTENCY PACKAGE

This invention relates to medical devices and methods and in particular to devices and methods for the impotence correction.

BACKGROUND OF THE INVENTION

In the human male as with many higher order animals, sexual performance involves three functions: erection, emission and ejaculation. A wide variety of medical or psychological problems can interfere with one or more of these functions. The inability to achieve and erection is referred to a impotency.

The principal methods presently used for impotence correction and treatment include: the use of psychiatric and pharmacological treatments, injections of vasoactive drugs into the penis, plastic surgery of penis muscle tissue and prosthetics implantation. These prior art techniques only deal with the erection problem and do not provide the capability emission and ejaculation.

U.S. Pat. Nos. 5,246,015; 5,065,744 and 4,869,241 provide mechanical support for producing an erection. U.S. Pat. Nos. 5,236,904; 5,256,652 and 5,236,904 are the pharmaceutical type of impotence correction providing drugs administered to the penis.

What is needed is an effective device and method for correcting dysfunctional impotence which simulates the natural processes of erection and ejaculation as closely as feasible.

SUMMARY OF THE INVENTION

Present invention provides a device and method for impotence correction. An electronic device is implanted inside the body. It is programmable and controllable from outside the body. The press of a button sends an electronic signal which initiates a process which simulates the body's natural reproductive processes. In a preferred embodiment, a programmable electronic device is implanted under abdominal muscle rectus. An electrical conductor is stitched to the surface of the pelvic splanchnic nerve. Stimulation of this nerve by a series of low voltage electrical pulses from the electronic device causes dilation of the penis arteries which results in an erection. The electronic device is controlled by a controller operated by the patient or his partner. A second preferred embodiment also provides for emission stimulation. Emission is stimulated by electrical excitation of the pelvic plexus nerves from separate conductors from the electronic device. The device may be preprogrammed to set in motion the emission and ejaculation processes at appropriate time intervals after start of the erection process, or the device can be programmed to permit the patient (or his partner) to initiate the emission and ejaculation processes. In a third preferred embodiment a drug such as papaverine is administration from a storage chamber in the device. The drug is transmitted via a tube to the penis. As with the first two embodiments control is in the hands of the patient. Additional embodiments of the present invention are represented by various combinations of the above described embodiments.

DETAILED DESCRIPTION OF PREFERRED EMBODIMENTS

Preferred embodiments of the present invention can be described by reference to the figures.

NATURAL INSEMINATION

Figures 1, 2:
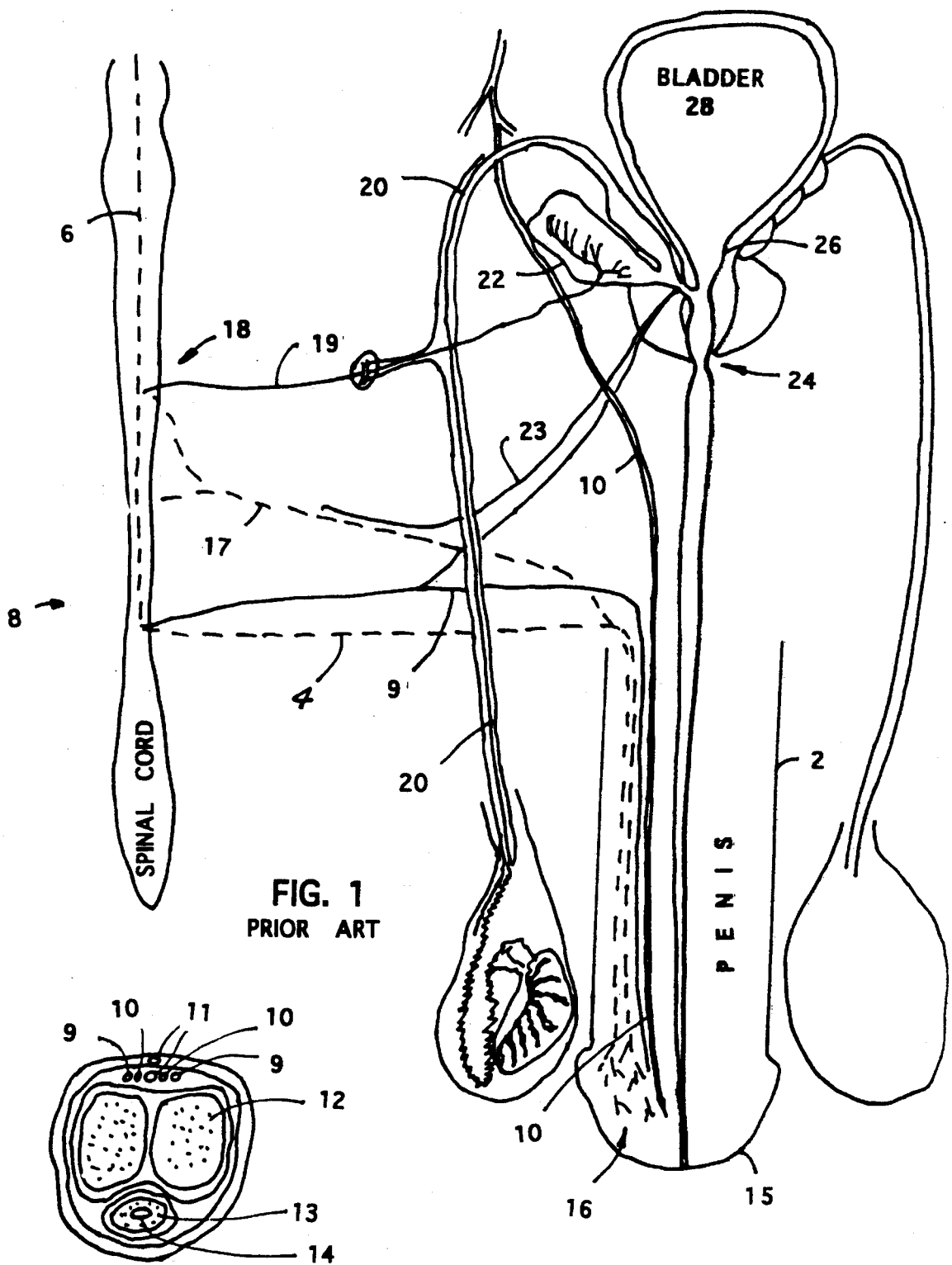
FIG. 1 is a drawing describing how God designed the human male reproductive system.
FIG. 2 is a drawing of the cross section of a human penis.

The natural interrelated mechanisms involved in the deposition of semen in the vagina by the natural means of copulation can be described by reference to the diagram in FIG. 1.

ERECTION

Erection of the penis 2 is generally a necessary prerequisite for penetration of the vagina. The stimuli for this reflex may involve either peripheral nerve receptors on or around the penis or mental stimulation. The stimuli are in the form of electrical signals. These signals are transmitted via routes 4 and 6, respectively, to central connections located in the sacral part of the spinal cord as shown at 8. From these central connections electrical signals are transmitted via the pelvic splanchnic nerves (the nervi ergentes) 9 to the penis. The pelvic splanchnic nerves provide electrical signals to the penis arteries (including the dorsal artery 10 shown in FIGS. 1 and 2 and a very large number of smaller arteries inside the penis). These electrical signals result in a dilation of the arteries permitting an increase of blood flow into the penis which in turn increases the blood pressure which has the effect of partially restricting the veins 11 (including the dorsal veins shown in FIGS. 1 and 2 ) taking blood out of the penis. As a result there is a rapid filling of blood spaces in the corpora cavernosa 12 and corpus spongiosum 13 areas of the penis. The net effect is erection. FIG. 2 shows a cross section view of the penis including the corpora cavernosa 12 and corpus spongiosum 13. Also shown are the two limbs of the dorsal artery 10 and the dorsal nerve 9, side by side at the top of the penis, the dorsal veins 11 and the urethra 14.

EMISSION

Emission is the movement of spermatozoa and secretions from the testes and other accessory glands into the urethra. This is entirely a reflex process. The afferent side of the reflex arc is initiated by touch receptors in the genital area such as receptors in the penis glans 15. In coming electrical signals travel via the pudendal nerves 17 to central relays in the upper lumbar segments 18 of the spinal cord. From there electrical signals travel via the pelvic plexus nerves 19 to stimulate parasympathetic fibres which in turn stimulate the ductus deferens 20 to slowly pump sperm and the seminal vesicles 22 to slowly pump siminal fluid into the urethra.

EJACULATION

Ejaculation is the propulsion of semen out of the urethra. The same afferent paths are involved. Central connections are located in the lower lumbar and upper sacral segments of the spinal cords. Efferent stimuli are conveyed by parasympathetic fibres of the pelvic splanchnic nerves 9 and by somatic motor fibres 23 in the pudendal nerves 17. Ejaculation is caused by the rhythmic contraction of the bulbocavernosus muscles 24, while the internal vesicle sphincter 26 closes to prevent retrograde ejaculation into the bladder 28.

FIRST PREFERRED EMBODIMENT

Figure 3:
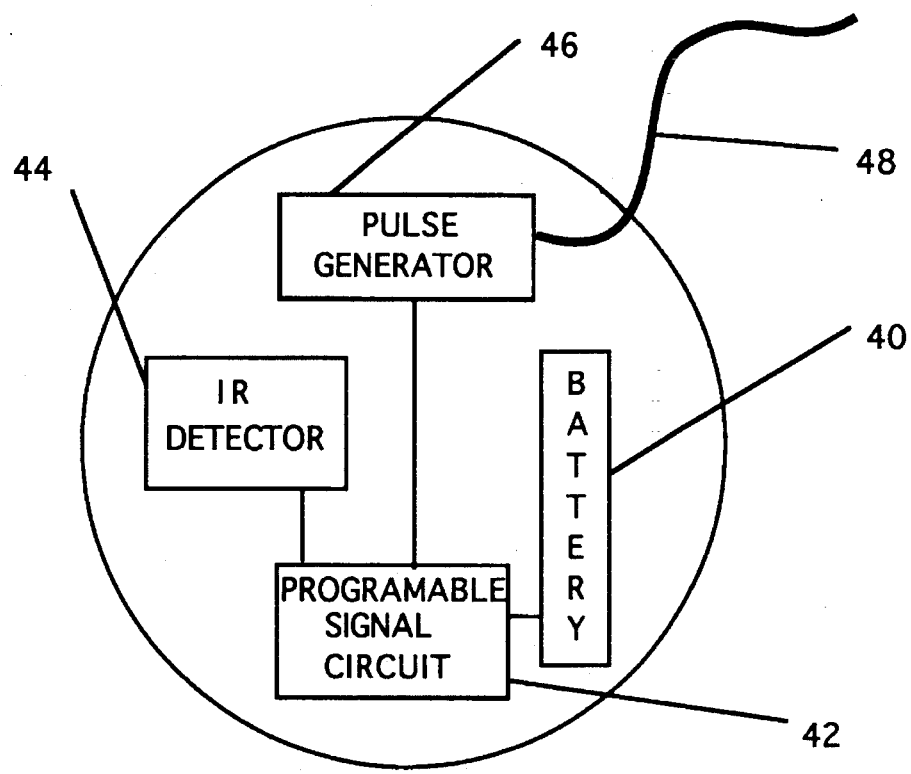
FIG. 3 is a drawing of a signal generator portion of a first preferred embodiment of the present invention.
Figure 4:
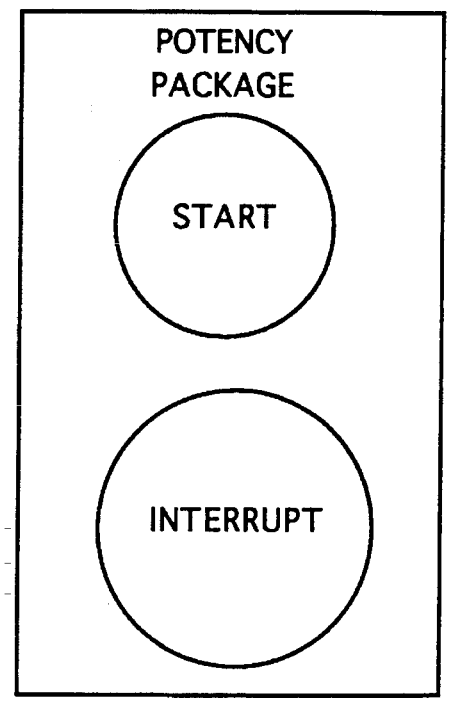
FIG. 4 is the control unit of the device in FIG. 3.
Figure 5:
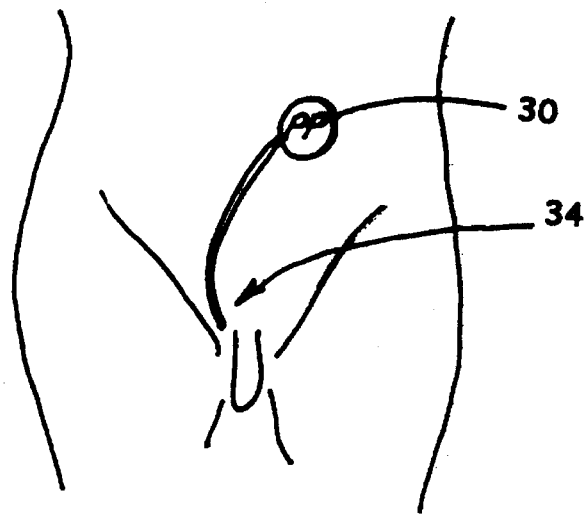
FIG. 5 shows a preferred placement of the above first preferred embodiment in a human male.
Figure 6:
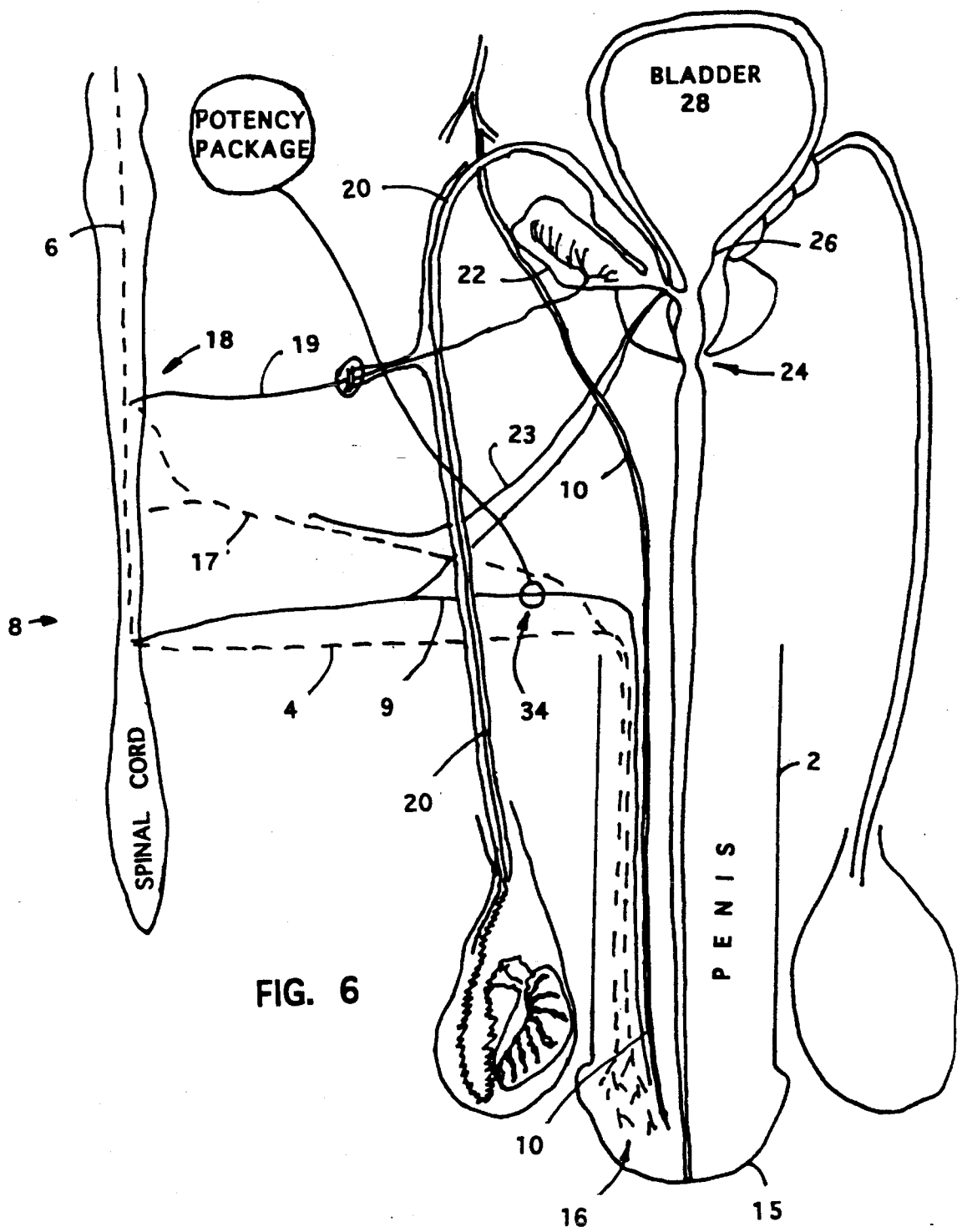
FIG. 6 shows the function of the males reproductive system with the above preferred embodiment.
Figure 8:
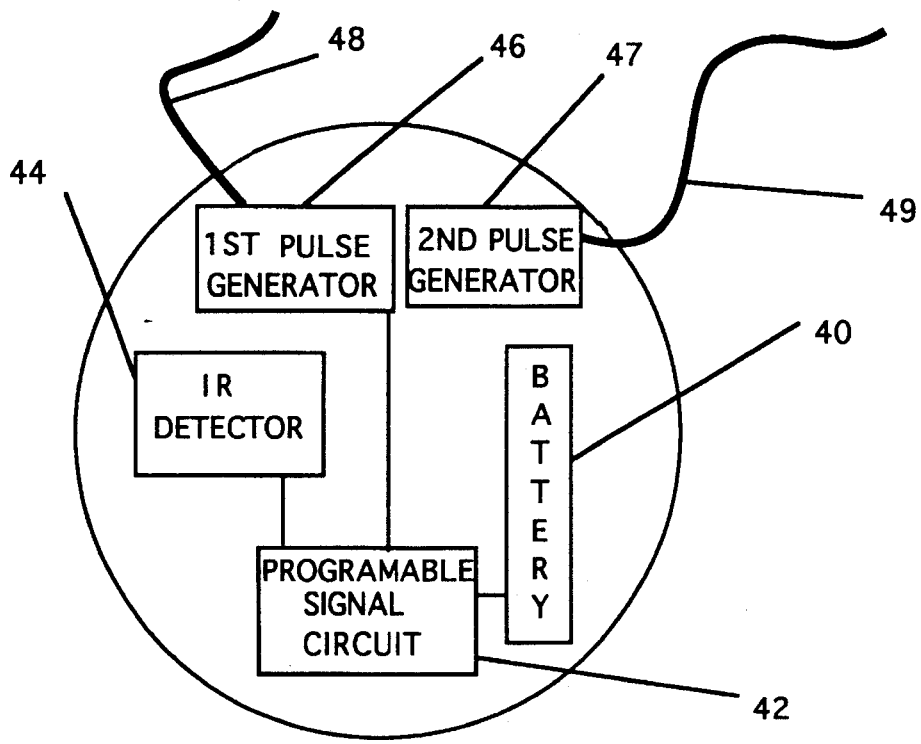
FIG. 8 shows a signal generator portion of a second preferred embodiment.
Figure 12:
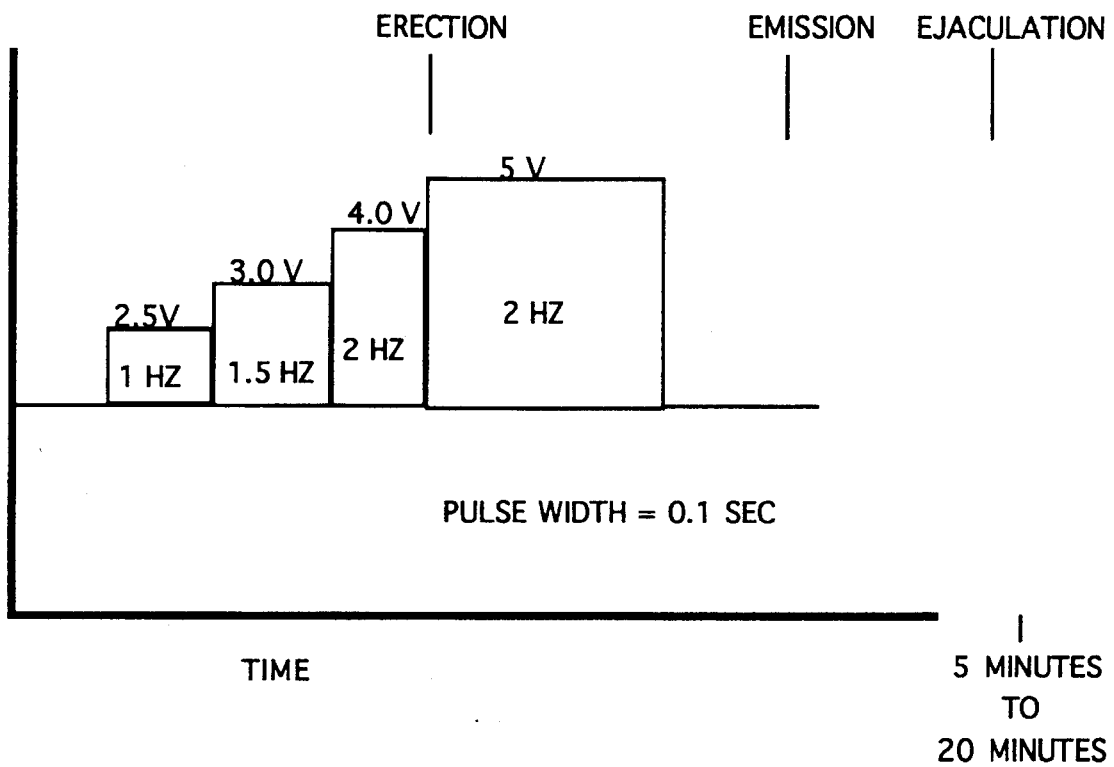
FIG. 12 shows a preferred pulse program for the FIG. 3 device.

FIG. 3 is a block diagram of a device which the Inventors call a potency package. A preferred prototype embodiment comprises a modified commercial pacemaker Model 600AV manufactured by Seimens. The device is designed to be installed under the patient's abdominal muscle rectus, but it could be installed in several other convenient places. The unit comprises battery 40, programable signal circuit 42, infrared detector 44 and pulse generator 46. The unit is controlled with an external control unit shown in block diagram for in FIG. 4. The unit comprises a start button and an interrupt button. A preferred sequence of pulses which should provide good results for many patients is shown in FIG. 12. The package can be reprogrammed to change any of the parameters shown in FIG. 12 which are pulse height, pulse width, frequency, duration and sequence. The best program for each individual patient can only be determined by testing. These parameters such as number of pulses group, voltage, pace, pulse duration are well within the ranges available with the above Seimens device. These parameters and any others within the range of the device can be programmed into it with commercially available pacemaker programmer such as Model #3CMHK 850 supplied by MIFI. The programmer transmits programming information via a pulsating magnetic field generated in the programmer to an electromagnetic detector in programmable signal circuit 42. This device shown in FIG. 3 comprises one electrode 48. The electrode should preferably be run from under the just patient's abdominal muscle rectus at position 30, under the abdominal skin tissue to location 34 as shown in FIG. 5 and there connect with the pelvic splanchnic nerves 9. The pelvic splanchnic nerve is located about one centimeter under the skin at the location shown on FIG. 5. The procedure can be accomplished in a medical doctors office or hospital, under local anesthesia. The nerve is located by a 5 cm incision at location 34. The nerve may be clamped between electrode leads as shown in FIGS. 6A and 6B. (Persons skilled in the art will recognize that many other surgical techniques for connecting electrodes to nerve tissue could be used.)

The recommended electronic pulse series is shown in FIG. 5. If this series does not produce the desired effect, the doctor can vary the parameters. If an erection is produced by any of the tests, then the doctor continues the process and installs the potency package as described above. If the doctor is unable to produce an erection, he may choose not to proceed with the operation.

SECOND PREFERRED EMBODIMENT

Figure 7A:
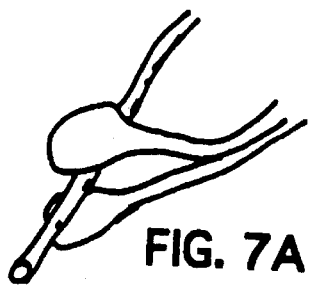
FIGS. 7 A and B show a preferred method of connecting electrodes to nerve fibers.
Figure 7B:
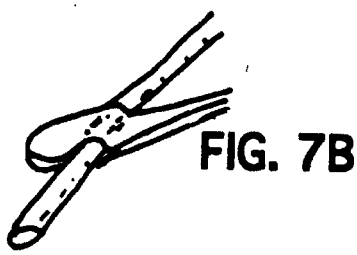
Figure 11:
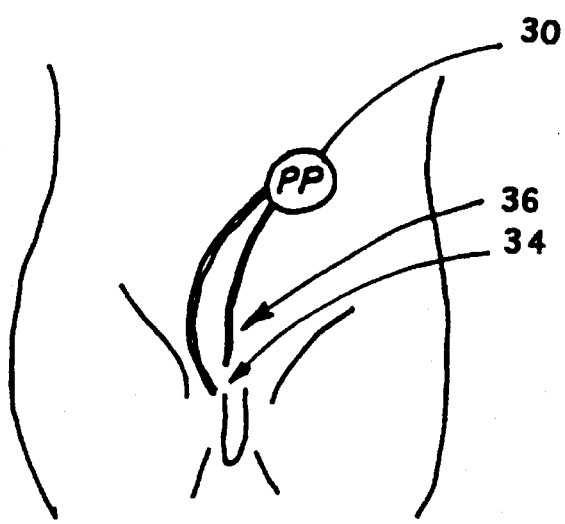
FIG. 11 shows where to connect the electrodes from signal generator shown in FIG. 7.
Figure 9:
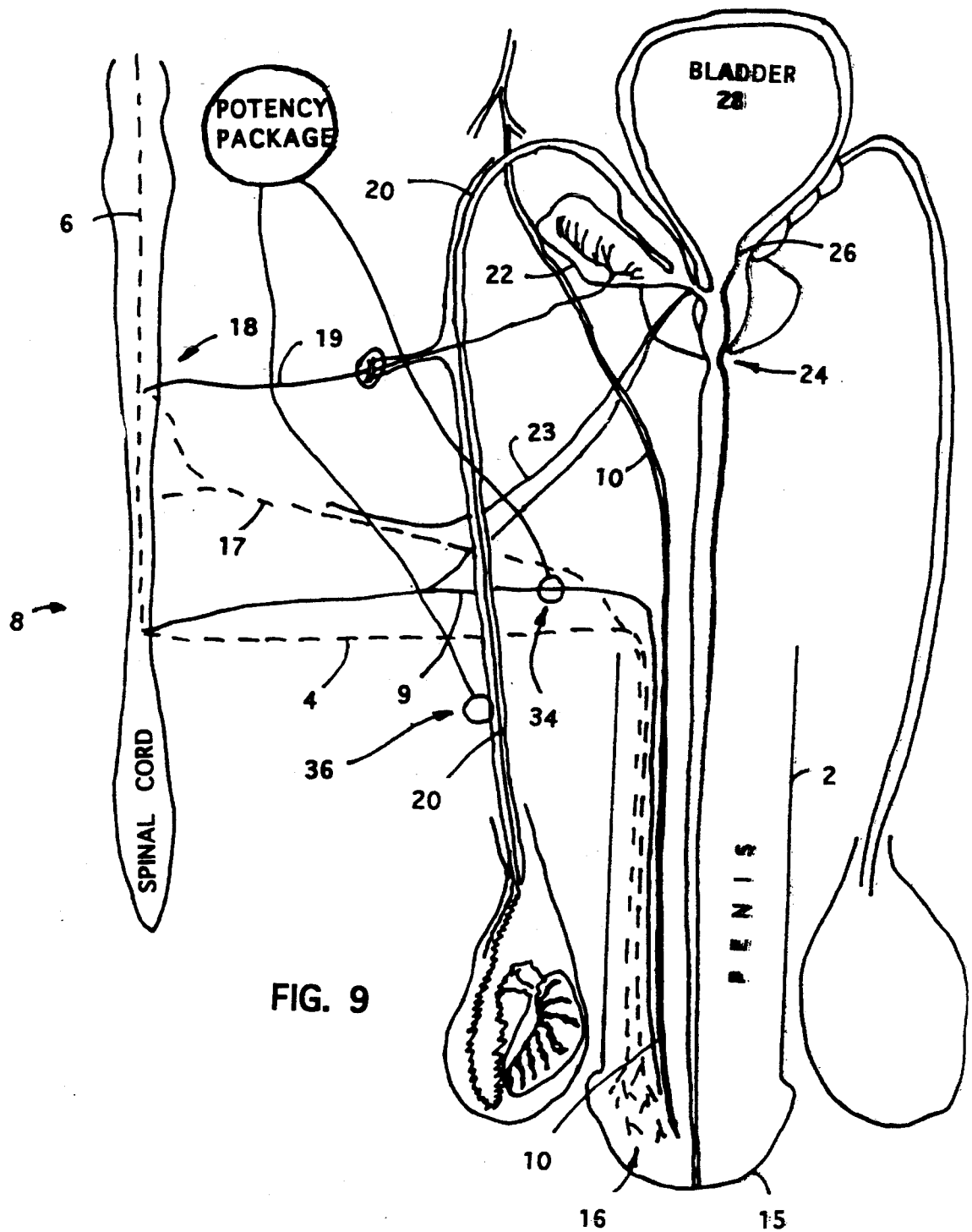
FIG. 9 shows the function of the males reproductive system with the second preferred embodiment.

A second preferred embodiment of our potency package is shown in FIG. 7. This embodiment is just like the first embodiment except the potency package comprises a second pulse generator 47 which is programmed to simulate emission. A second electrode 49 from the device is connected to the pudendal nerves 17 at location 36 as shown in FIG. 9. Location 36 is also shown on FIG. 11. This nerve can most easily be reached by making a 1 cm incision of the skin in the pubic area just at the location shown at 36 in FIG. 11. Then make an incision of the rectal muscle ligament and reach the nerve-vessel-ductus deferens bundle. Make a 0.5 cm incision in the cover of the bundle and attach the electrode to the pelvic plexus nerve. The place of attachment is also shown in FIG. 9 at 36.

Figure 13:
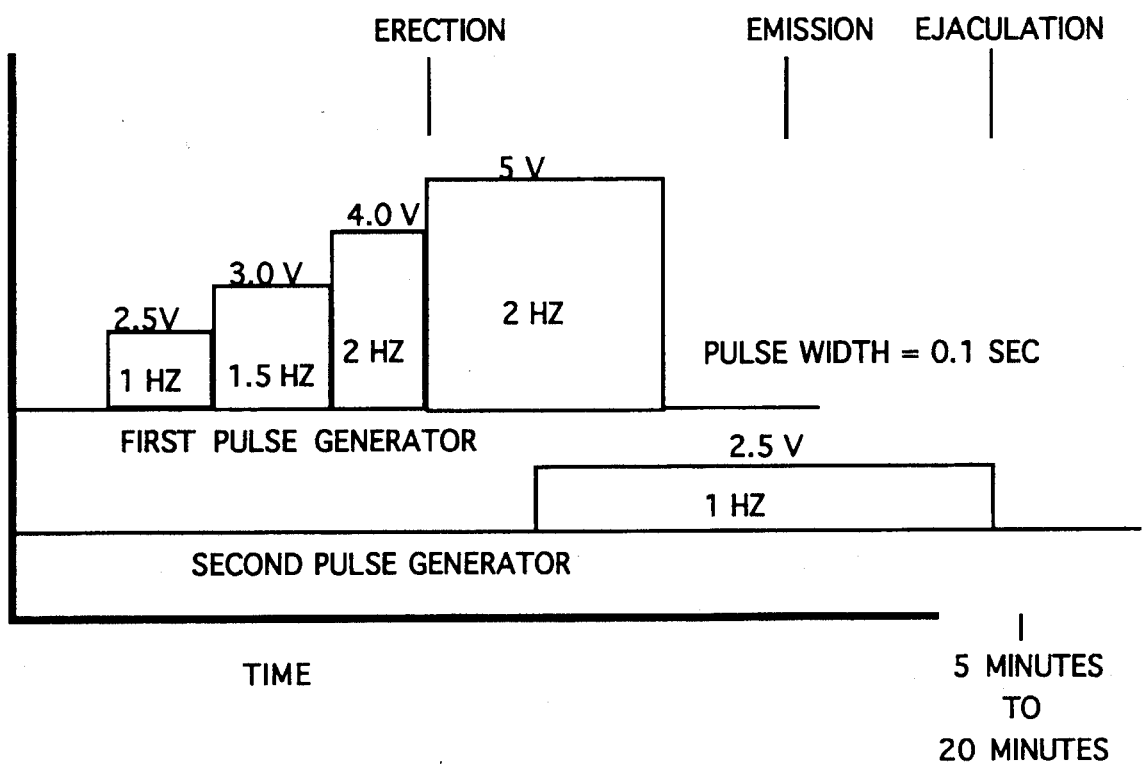
FIG. 13 shows a preferred pulse program for the FIG. 8 device.

As above, if the doctor is uncertain if the patient is a good candidate for the procedure, Applicants recommend that a patient be tested prior to installation of the device to determine if the emission can be stimulated the particular patient. Applicants recommend that initially the potency package be programmed to produce the pulse trains shown in FIG. 13

THIRD PREFERRED EMBODIMENT

Figure 10:
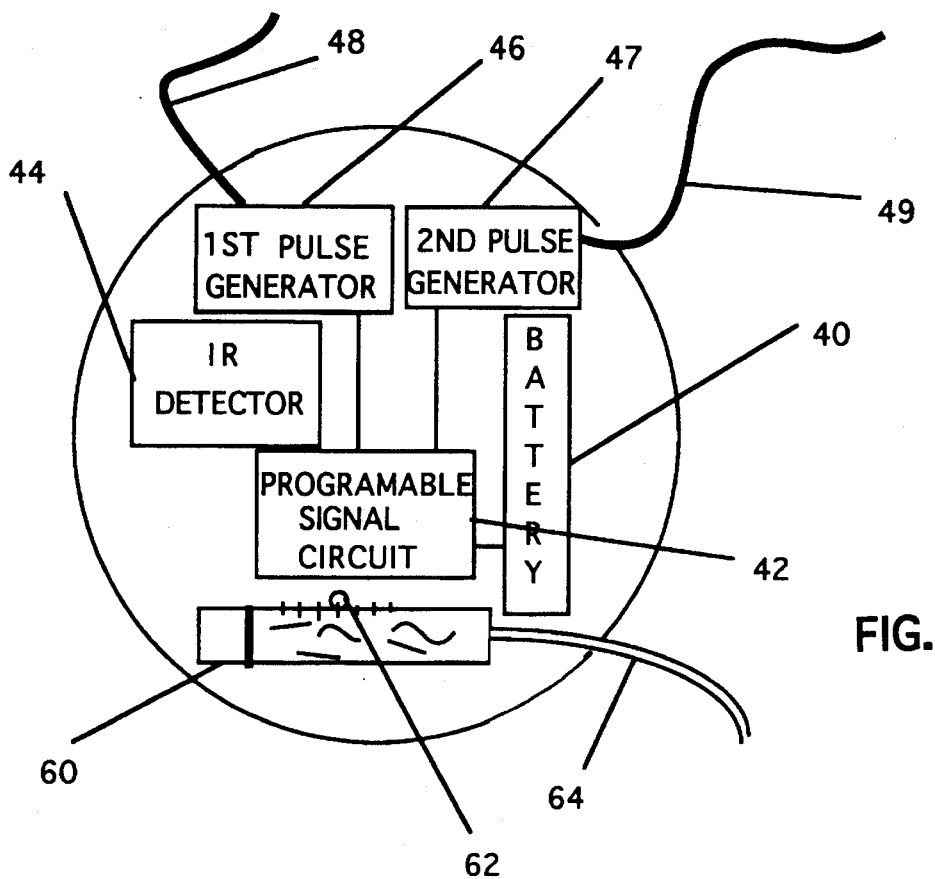
FIG. 10 shows a third signal generator, also incorporating a drug dispenser feature.

In this embodiment the device, shown in FIG. 10 contains a chamber 60 for storage within the body of a suitable drug such as papaverine, a small electronic pump 62 and a very thin tube 64 for delivering the drug to the penis. The tube is run under the skin of the abdomen to the upper part of the penis. The tube then branches into 3 branches, one each to the two corpora cavernosa and one for the corpus spongiosium. As with the two previously described embodiments, the delivery of the drug is initiated by an electronic signal transmitted by a hand held transmitter within the control of the patient. For this embodiment the two electronic circuits are programmed as described for the second preferred embodiment as described above. The potency package is programmed to deliver the drug at time zero.

Drug delivery chambers consists of a plastic refillable containers which is placed into hermetic chamber 62. The bottom of the chamber is a piston with a coil and electromagnet step driver. As the first step of the erection stimulation is a vasoactive drug delivered by sending an electrical potential to the driver. The driver pulls the coil into the electromagnet up to a definite distance squeezing the drug into the tube attached to the plastic container with one end and implanted into cavernous bodies of the penis at the other end of the tube. The other drug chambers for various health condition correction are built similarly. They are refillable as well by injection through the skin with a syringe injector.

EQUIPMENT

The potency package components can be standard off-the-shelf components. The components include: a lithium battery LBSAR 5 made by SARATOF with a lifetime of 5 to 8 years, a pulse generator CLG 445 made by MIFI, a receiver/transmitter MC145027 made by Motorola and IR remote control receiver U338M made by AEG Corporation, a fast IR photodiode detector s1133-11 made by Hamamatsu, IR remote control transmitter U327M made by AEG Corporation, stepping motor 155 NL Micro Slide made by Toshiba Corporation, silicon tubing catheter T5715 made by Dow Corning Silasastic and elastomer Q7-4750 silicon pack made by Dow Corning Silastic.

THE SURGERY

The surgery to provide implantation is described with respect of the sixth embodiment which includes electrodes for erection and for emission and a thin tube for drug delivery to the penis. The potency package should be surgically implanted by a trained physician. The operation is very similar to the implantation of a heart pacemaker. A skin dissection is performed on the alba line below the umbilical. The peritoneal cavity is dissected and the path to the retroperitoneal is opened on the level of L4-S2. The electrodes are passed from the retroperitoneal to the subcutaneous layer of the frontal abdominal wall, where they are connected with the stimulator. Using micro surgical techniques, the carbonic electrode 28 is sewn to the parasimpatic nerve fiber and carbonic electrode 30 is sewn to the simpatic nerve fiber. The electrodes are passed from the retroperitoneal to the subcutaneous layer of the frontal abdominal wall where they are connected with the chambers 10 and 12 of the potency package. The tube carrying the drug is connected to the corpora cavernosa so as to deliver this drug to directly to the penis. The potency package is implanted subcutaneously to the frontal abdominal wall either to the right or to the left above the umbilical. The package has no contact with the operational wound. The wound is sewn layerly.

OTHER EMBODIMENTS

Many other embodiments of the present invention are provided by various combinations of the above described embodiments. A forth embodiment would provide for emission stimulation only, a fifth is drug only.

The following table lists vasoactive drugs and recommended quantities:

| Vasoactive Agent | Average Dose per Injection |
| --- | --- |
| Papaverine | 15 mg |
| Phentolamine | 0.5 mg |
| Prostaglandin E1 | 20 μg |
| Vasoactive Intestinal Polypeptide | 5 μg |

Additional embodiments are provided by providing more than one drug. For example a drug such as nitroglycerine could be provided to be released into the blood stream to provide protection of patients against heart attack during sex. The following table shows some drugs recommended for the correction of health conditions which are the most common appeared during sex intercourse.

| Health Condition | Medication |
| --- | --- |
| Arrhythmia | Beta-blockers |
| Asthma | Alpha-blockers |
| Angina | Nitroglycerin |
| Hypertension | Vasodilators |

Additional embodiments are provided by using many different drugs which are known to induce erection. Also, there are many electronic pulse sequences which would work well to produce erection, emission and ejaculation for many different patients in addition to the sequences described above. Electrodes may also be provided to stimulate the penal muscles. Medical doctors will recognize that electrodes can be connected at many locations other than the ones shown.

To correct the arterial circulatory problem of impotence the arterial anastamosis should be performed at the same time as potency pack implantation. Anastomosis between inferior hypogastric artery and the central and dorsal artery and dorsal vein of penis is preferable.

DIABETIC TYPE OF IMPOTENCE CORRECTION

To correct the diabetic circulatory problem of impotence the arterial anastamosis should be done as distal to the penile glans as possible and same time as potency pack implantation. Anastomosis between the hypogastric artery and dorsal artery end-to-end or end-to-side. Penile veins of diabetic patients could usually provide blood flow and their surgical correction is not required in most cases.

ANIMAL USE

The teachings of the present invention can be applied to many animals other than man. It should be especially valuable for use with breeding animals such as prize bulls. It could also be used in the breeding programs of captured members of endangered species of wild animals.

While the above description contains many specificities, the reader should not construe these as limitations on the scope of the invention, buy merely as exemplifications of preferred embodiments thereof. Those skilled in the art will envision many other possible variations are within its scope like pacemaker implantation in other location than under the rectal muscle of abdomen, design different types of electrodes and pacemakers, to use different voltage, amplitude, pulse group, repetition rate, pulse duration, remote control with more or less functions, fully automatic preprogrammed pacemaker without external control, etc. Persons skilled in art will recognize that the teachings of this invention can be applied to treat frigidity in women by clitoris erection stimulation. In this case an electronic device is provided with two electrodes: one provides for erection of the clitoris and the other for pudendal muscle contraction around the vaginal entrance. Other elements in the women's device might provide for an electrode for urethra muscle contraction for urine incontinence correction during sexual intercourse. Accordingly the reader is requested to determine the scope of the invention by the appended claims and their legal equivalents, and not by the examples which have been given.

We claim:
1. A device for the cure of impotency comprising:
   a) an electronic exciting means for providing stimulation to a sex organ of a male human, said means being surgically installed under the skin of said male human,
   b) a transmitting means for transmitting said stimulation from said exciting means to said sex organ,
   c) a means for programming said exciting means,
   d) an electronic control means for controlling said exciting means so as to initiate and control said stimulation.
2. A device as in claim 1 wherein said electronic exciting means comprises at least one electronic pulse generator.
3. A device as in claim 2 wherein said transmitting means comprises an electrode connecting said electronic exciting means to pelvic splanchnic nerve of said male human.
4. A device as in claim 2 wherein said transmitting means comprises an electrode connecting said electronic exciting means to pelvic plexus nerve of said male human.

5. A device as in claim 3 wherein said electronic exciting means is programmable to produce electrical pulses.

6. A device as in claim 4 wherein said electronic exciting means is programmable to produce electrical pulses.

7. A device as in claim 2 wherein said at least one pulse generator is two pulse generators and said transmitter means comprises a first electrode connecting said electronic exciting means to pelvic plexus nerve of said male humans and a second electrode connecting said electronic exciting means to pelvic plexus nerve of said male human.

8. A device as in claim 1 wherein said electronic exciting means comprises a storage vessel for the storage of a vasoactive drug and said transmitting means comprises a thin tube for transmitting said vasoactive drug to the penis of said human male.

9. A device as in claim 2 wherein said at least one pulse generator is two pulse generators and said transmitter means comprises a first electrode connecting said electronic exciting means to pelvic plexus nerve of said male humans and a second electrode connecting said electronic exciting means to pelvic plexus nerve of said male human, and wherein said electronic exciting means also comprises a storage vessel for the storage of a vasoactive drug and said transmitting means comprises a thin tube for transmitting said vasoactive drug to the penis of said human male.

10. A method of correcting impotency in a male animal comprising the steps of:

a) surgically implanting under the skin of said male animal a programmable electronic stimulation means, b) surgically implanting a transmitting means for transmitting a stimulation from said exciting means to a sex organ of said male animal, c) providing a means for programming said programmable electronic stimulation means, d) providing said male animal with an electronic control means for controlling said exciting means so as to initiate and control said stimulation so as to produce erection, emission and ejaculation.

11. A method as in claim 10 wherein said male animal is a domesticated animal.

12. A method as in claim 10 wherein said male animal is a captured wild animal.

13. A method as in claim 10 wherein said male animal is a human.

14. A device for the cure of impotency comprising:

a) an electronic exciting means for providing stimulation to a sex organ of a male animal, said means being surgically installed under the skin of said male animal, b) a transmitting means for transmitting said stimulation from said exciting means to said sex organ, c) a means for programming said exciting means, d) an electronic control means for controlling said exciting means so as to initiate and control said stimulation.

* * * * *